(12) United States Patent
Åkerfeldt

(10) Patent No.: US 7,135,032 B2
(45) Date of Patent: Nov. 14, 2006

(54) FEMORAL COMPRESSION DEVICE WITH SUPPORT

(75) Inventor: Dan Åkerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 414 days.

(21) Appl. No.: 10/235,859

(22) Filed: Sep. 6, 2002

(65) Prior Publication Data

US 2004/0049214 A1    Mar. 11, 2004

(51) Int. Cl.
*A61F 5/34* (2006.01)
*A61B 17/00* (2006.01)

(52) U.S. Cl. .................. 606/203; 606/201; 606/151

(58) Field of Classification Search .... 606/201–204.55
See application file for complete search history.

(56) References Cited

U.S. PATENT DOCUMENTS

| 3,884,240 | A |   | 5/1975  | Gilman |         |
|-----------|---|---|---------|--------|---------|
| 5,307,811 | A | * | 5/1994  | Sigwart et al. | 600/490 |
| 5,569,297 | A | * | 10/1996 | Makower et al. | 606/201 |
| 5,728,120 | A |   | 3/1998  | Shani et al. |       |
| 6,264,673 | B1 | * | 7/2001 | Egnelov et al. | 606/201 |

FOREIGN PATENT DOCUMENTS

| EP | 0 462 088 B1 | 11/1995 |
|----|--------------|---------|
| JP | 05-154160 A  | 6/1993  |
| SE | 9002077      | 6/1990  |
| SE | 9003271      | 10/1990 |

* cited by examiner

*Primary Examiner*—Glenn K. Dawson
(74) *Attorney, Agent, or Firm*—Foley & Lardner LLP

(57) ABSTRACT

A femoral compression device includes a pressure applying device for compressive bearing at a puncture site at a femoral artery of a patient and for applying pressure on the puncture site, a belt adapted to be fixed around the patient's body, and a base plate provided with first and second extensions, with the end of the first extension being closer to the pressure applying device than the end of the second extension and being provided with a fastener in the ends thereof for fastening of an end of the belt. The compression device also includes a support plate, which is attached to the second extension and which is adapted to bear against the patient's body, thereby compensating for the imbalance, which originates from the different extents of the two extensions, that otherwise would be present.

11 Claims, 1 Drawing Sheet

FEMORAL COMPRESSION DEVICE WITH SUPPORT

BACKGROUND

The present invention relates generally to a femoral compression device comprising a pressurizing (or pressure applying) means that presses against the femoral artery, and in particular to a femoral compression device comprising two extensions with different lengths and an extra support that in use compensates for the imbalance of the device.

The present invention is an improvement of the femoral compression device disclosed in the patents U.S. Pat. No. 5,307,811 and EP 0 462 088, which are assigned to the present assignee and which claim priority from SE 9002077 and SE 9003271. All four of these documents are incorporated herein by reference in their entirety. A femoral compression device according to these publications comprises basically a pressurizing means for compressive bearing against a puncture site at a femoral artery of a patient, a belt adapted to be fixed around the patient's body, and a base plate supporting the pressurizing means and being provided with two extensions. In use, the pressurizing means, which in one embodiment has the form of an inflatable semi-spherical air cushion, is positioned over the femoral artery, and the belt, which extends from the end of the first extension, around the patient's body and to the end of the second extension, is tightened.

SUMMARY OF THE INVENTION

Because of the position of the femoral artery, i.e. at one of the patient's groins and not in the centre of the body, the two extensions have different lengths. This means that the moment arm from the end of the first extension to the centre of the inflatable air cushion differs from the corresponding moment arm of the second extension. In other words, this prior art femoral compression device exhibits an inherent imbalance, which strives to tilt the compression device and which can make the inflatable air cushion move away from the puncture site, thereby causing unnecessary bleeding.

An object of the present invention is therefore to provide an improved femoral compression device which during use presses against the femoral artery of a patient without showing any tendencies to tilt, which makes such a compression device more user-friendly and eliminates the risk that the inflatable air cushion moves away from the wound site.

This object is achieved by a femoral compression device that is provided with a support plate at the end of the longest extension. In use, the support plate bears against the body of a patient, and counteracts the force that acts to tilt the compression device. In a preferred embodiment of the present invention, the ends of the two extensions are in level, or almost in level, with the top of the expanded air cushion. With this design, the inherent imbalance of the femoral compression device has been compensated, and the tendency of the femoral compression device to tilt has thereby been eliminated.

DETAILED DESCRIPTION OF THE PREFERRED EMBODIMENTS

Figure 1:
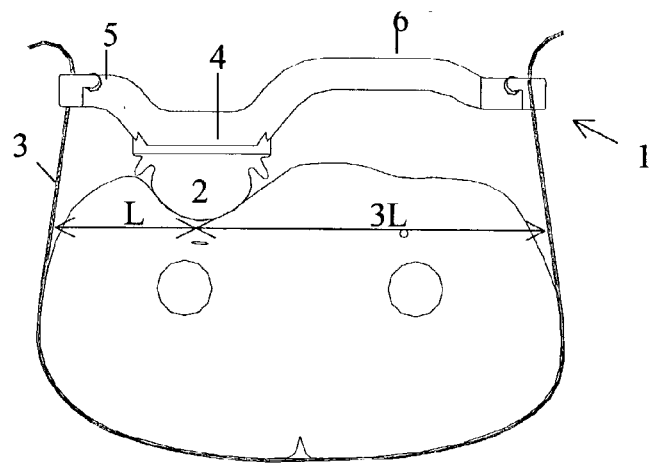
FIG. 1 is a cross-sectional view of a prior art femoral compression device attached to the body of a patient.

A prior art femoral compression device 1 is illustrated in cross-section in FIG. 1, where the compression device 1 is attached to the body of a patient. The compression device 1 comprises basically an inflatable air cushion 2, a belt 3, and base plate 4 provided with two extensions 5 and 6, which extend in opposite directions. In use, the belt 3 extends around the patient's body and is attached to the ends of the two extensions 5, 6. As can be seen from the figure, the first extension 5 is shorter than the second extension 6, which is due to the off-centre position of the femoral artery on which the air cushion 2 is intended to press.

In the exemplifying embodiment illustrated in FIG. 1, the distance from the end of the first extension 5 to the centre of the air cushion 2 is L, while the length from the end of the second extension 6 to the centre of the air cushion 2 is 3L. When the femoral compression device 1 is in its correct horizontal position, as shown in the figure, it follows therefore from the equation of moments that the force from the belt 3 that acts on the shorter first extension 5 is three times the force acting on the longer second extension 6. Clearly, if there were no friction acting between the skin at the back of the patient's body and the belt 3, this difference in the magnitudes of the two forces that act on the belt 3 from the extensions 5 and 6 would tilt the compression device 1.

Figure 2:
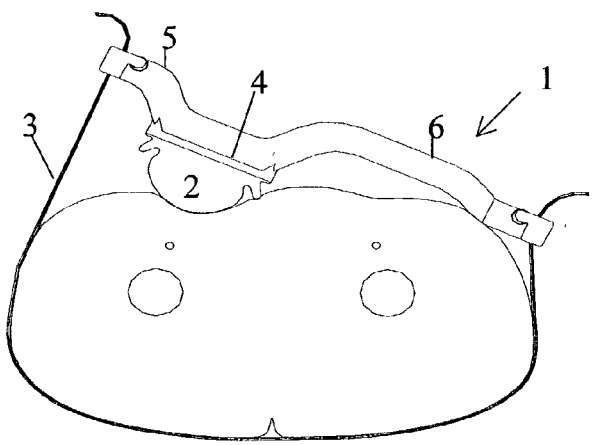
FIG. 2 is a cross-sectional view of the device of FIG. 1 in a tilted position.

FIG. 2 illustrates a hypothetical situation in which there is no friction that compensates for the difference in the magnitudes of the forces that act on the belt 3. As pointed out above, such friction is required to keep the compression device 1 in the horizontal position. When there is no friction acting between the belt 3 and the skin of the patient, the tensile force in the belt 3 is the same throughout its length, and, in particular, the force acting on the end of the first extension 5 is the same as the force acting on the end of the second extension 6. Normally, such a friction is present between the patient's skin and the belt 3, but the harder the belt is tightened, the greater is the strain on the skin, which can be uncomfortable for the patient. Besides being uncomfortable for the patient, this inherent imbalance of the prior art compression device 1, i.e. that its correct horizontal positioning relies on the friction between the skin and the belt, can lead to difficulties in the positioning of the compression device 1, which, in turn, may cause the air cushion 2 to move away from the wound site and thereby lead to unnecessary bleeding.

Figure 3:
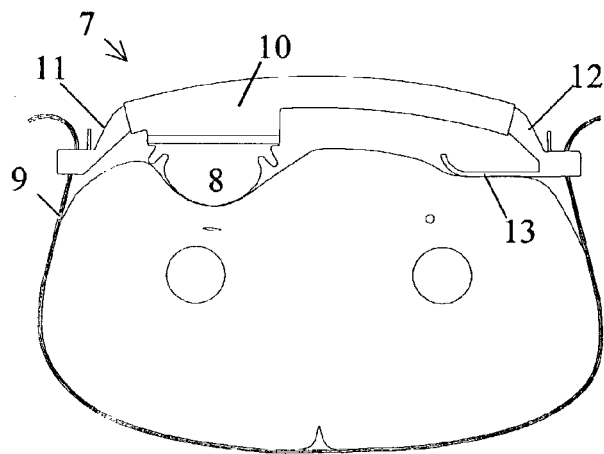
FIG. 3 is a cross-sectional view of a femoral compression device according to the present invention.

In FIG. 3 is illustrated a femoral compression device 7 according to the present invention. The compression device 7, which in the figure is attached to a body of a patient, comprises basically one and only one pressurizing (or pressure applying) means 8, a belt 9, and a base plate 10, which is provided with two extensions 11, 12 and a support plate 13. In this embodiment, the pressurizing means 8 is in the form of an inflatable air cushion 8, but it should be understood that other types of pressurizing (or pressure applying) means could be used, such as a cushion, a semi-rigid member, a rigid member, or a piston assembly. As in the prior art design, the first and second extensions 11, 12 extend in opposite directions, with the end of first extension 11 being closer to pressurizing means 8 than the end of second extension 12. The ends of the extensions 11, 12 are provided with locking means for insertion of the respective end of the belt 9, so that the belt 9 can be tightened around the patient's body. Here it should be mentioned that other means for fastening the belt to ends of the extensions could be provided. For example, the ends of the extensions could be provided with small hooks which engage in loops in the material of the belt, so that a Velcro® type of fastening means is provided, or the belt could be attached to the ends of the extensions by means of a suitable adhesive, or a combination of these means could be used. In use, the support plate 13, which is attached at the end of the longer second extension 12, compensates for the imbalance of the compression device 7 that would be present without the support plate 13. This means that even if there were no friction acting between the patient's skin and the belt 9, the compression device 7 would still maintain its correct horizontal position, since there exist no longer two opposing moment arms having different lengths with respect to a common point, i.e. the centre of the air cushion 8.

Preferably both (but at least one, in this embodiment) of the first and second extensions 11, 12 are telescopic in that they can telescope into and out from the base plate 10, thereby providing the compression device 7 with a variable length, so that the support plate 13 can be accurately positioned at a site over the one of the two groins where there is no puncture wound. It should also be noted that—in contrast to the design shown in FIG. 1 and FIG. 2—the base plate 10 as well as the first and second extensions 11, 12 have curved shapes, with the ends of the first and second extensions 11, 12 being well below the level of the base plate 10, i.e. almost in level with the top of the inflated air cushion 8. This design has shown to provide the patient with the best comfort, and together with the support plate 13 eliminates all tilting tendencies of the compression device 7. Here it could be mentioned that the exact level of the ends of the first and second extensions depends on the specific design of the compression device, i.e. the curvature of the base plate, as well as on how much the extensions have been drawn out from the base plate, but the ends of the extensions should at least be below the level of the base plate and preferably be in level, or almost in level, with the top of the expanded pressurizing means.

Figure 4:
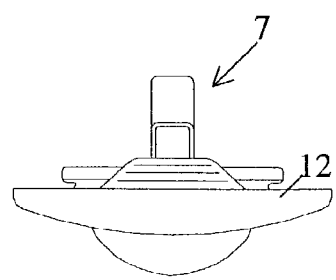
FIG. 4 is an end-view of the femoral compression device of FIG. 3.

The support plate 13 can have different shapes, but it should preferably have a shape that corresponds to the body contour at the site over the groin against which it will bear. FIG. 4 shows an end-view of the compression device 7. It can be seen from the figure that the end of the second extension 12 has been given a slightly curved shape, and, although not explicitly visible in the figure, the support plate 13 has a corresponding curved shape. These curved shapes of the second extension 12 and the support plate 13 provide the patient with the best comfort, and give the patient a possibility to rise to a sitting position without risking that the compression device 8 moves away from its correct position. The material in the support plate 13 should preferably have some flexibility, but should, of course, not be so flexible that it cannot provide the necessary support that counteracts the force from the belt 9.

Although the present invention has been described with reference to a specific embodiment, also shown in the appended drawings, it will be apparent for those skilled in the art that many variations and modifications can be done within the scope of the invention as described in the specification and defined with reference to the following claims.

What is claimed is:

1. A femoral compression device comprising:
    a single inflatable pressure applying device adapted to apply pressure at a puncture site at a femoral artery of a patient;
    a flexible member adapted to be fixed around the patient's body; and
    a base member provided with first and second extensions, with an end of the first extension being closer to the pressure applying device than an end of the second extension and being provided with a fastener to secure the flexible member,
    wherein the compression device also comprises a support member, which is attached to or near the second extension and which is adapted to bear against the patient's body,
    wherein the pressure applying device and the support member are arranged such that they bear against the same side of the patient's body when the femoral compression device is arranged around the patient's body;
    wherein the support member protrudes away from the second extension such that when the femoral compression device is arranged around the patient's body both the pressure applying device and the support member contact the body to maintain the first and second extensions substantially level;
    wherein the femoral compression device is configured to accommodate one and only one inflatable pressure applying device.

2. A femoral compression device according to claim 1, wherein at least one of the extensions is telescopic.

3. A femoral compression device according to claim 1, wherein the support member comprises a support plate which distributes pressure over the patient's body.

4. A femoral compression device comprising:
    a single inflatable pressure applying device adapted to apply pressure at a puncture site at a femoral artery of a patient;
    a belt adapted to be fixed around the patient's body; and
    a base plate provided with first and second extensions, with an end of the first extension being closer to the pressure applying device than an end of the second extension and being provided with a fastener in the ends thereof to fasten the belt,
    wherein the compression device also comprises a support plate, which is attached to the second extension and which is adapted to bear against the patient's body,
    wherein the pressure applying device and the support plate are arranged such that they bear against the same side of the patient's body when the femoral compression device is arranged around the patient's body;
    wherein the support plate protrudes from the second extension such that when the femoral compression device is arranged around the patient's body both the pressure applying device and the support plate contact the body to maintain the first and second extensions substantially level;
    wherein the femoral compression device is configured to accommodate one and only one inflatable pressure applying device.

5. A femoral compression device according to claim 4, wherein when the compression device is attached to the patient's body, the ends of the first and second extensions are below the other portions of the base plate.

6. A femoral compression device according to claim 5, wherein at least one of the extensions is telescopic.

7. A femoral compression device according to claim 4, wherein at least one of the extensions is telescopic.

8. A femoral compression device according to claim 4, wherein the support plate has a slightly rounded shape that corresponds to a contour of the patient's body at the site against which the support plate bears.

9. A femoral compression device according to claim 4, wherein the support plate has some flexibility.

10. A femoral compression device comprising:
a pressure applying device adapted to apply pressure at a puncture site at a femoral artery of a patient;
a flexible member adapted to be fixed around the patient's body; and
a base member provided with first and second extensions, with an end of the first extension being closer to the pressure applying device than an end of the second extension and being provided with a fastener to secure the flexible member,
wherein the compression device also comprises a support member, which is attached to or near the second extension and which is adapted to bear against the patient's body; and
wherein when the compression device is attached to the patient's body, the ends of the first and second extensions are approximately level with a patient-contacting portion of the pressure applying device.

11. A femoral compression device according to claim 10, wherein at least one of the extensions is telescopic.

* * * * *